(12) United States Patent
Mohideen et al.

(10) Patent No.: US 10,717,036 B2
(45) Date of Patent: Jul. 21, 2020

(54) METHOD USING METAL-ORGANIC FRAMEWORK COMPOSITIONS

(71) Applicant: King Abdullah University of Science and Technology, Thuwal (SA)

(72) Inventors: Mohamed Infas Haja Mohideen, Thuwal (SA); Karim Adil, Thuwal (SA); Youssef Belmabkhout, Thuwal (SA); Mohamed Eddaoudi, Thuwal (SA); Prashant M. Bhatt, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 100 days.

(21) Appl. No.: 15/770,808

(22) PCT Filed: Oct. 26, 2016

(86) PCT No.: PCT/IB2016/056435
§ 371 (c)(1),
(2) Date: Apr. 25, 2018

(87) PCT Pub. No.: WO2017/072673
PCT Pub. Date: May 4, 2017

(65) Prior Publication Data
US 2018/0264394 A1  Sep. 20, 2018

Related U.S. Application Data

(60) Provisional application No. 62/246,392, filed on Oct. 26, 2015.

(51) Int. Cl.
| | | |
|---|---|---|
| *B01D 53/04* | (2006.01) | |
| *B01D 53/047* | (2006.01) | |
| *B01J 20/28* | (2006.01) | |
| *B01J 20/22* | (2006.01) | |
| *B01J 20/30* | (2006.01) | |
| *C07C 45/78* | (2006.01) | |
| *B01D 53/02* | (2006.01) | |

(52) U.S. Cl.
CPC ........... *B01D 53/047* (2013.01); *B01D 53/02* (2013.01); *B01J 20/226* (2013.01); *B01J 20/2808* (2013.01); *B01J 20/3085* (2013.01); *C07C 45/78* (2013.01); *B01D 53/0462* (2013.01); *B01D 2253/204* (2013.01); *B01D 2256/24* (2013.01); *B01D 2257/304* (2013.01); *B01D 2257/504* (2013.01); *B01J 2523/17* (2013.01); *B01J 2523/27* (2013.01); *B01J 2523/845* (2013.01); *B01J 2523/847* (2013.01); *Y02C 10/08* (2013.01); *Y02E 50/346* (2013.01)

(58) Field of Classification Search
CPC .. B01J 20/226; B01J 20/2808; B01J 2523/17; B01J 2523/27; B01J 2523/845; B01J 2523/847; B01D 53/04; B01D 53/047; B01D 2253/204; B01D 2256/24; B01D 2257/304; B01D 2257/504
USPC ......................................................... 502/401
See application file for complete search history.

(56) References Cited

PUBLICATIONS

Notification of Transmittal of the International Search Report and the Written Opinion of the International Searching Authority, or the Declaration for PCT/IB2016/056435 dated Jan. 10, 2017.
Li, et al., "Metal-organic frameworks based upon non-zeotype 4-connected topology", Coordination Chemistry Reviews, vol. 261 Feb. 15, 2014, 1-27.
Ping, et al., "Multipoint interactions enhanced CO2 Uptake: A Zeolite-like zinc-tetrazole Framework with 24-Nuclear Zinc Cages", Journal of the American Chemical society, vol. 134, No. 46, Nov. 21, 2012, 18892-18895.
Wei-Xiong, et al., "Flexible mixed-spin Kagome coordination polymers with reversible magnetism triggered by dehydration and rehydration", Inorganic Chemistry, vol. 50, No. 1, Nov. 3, 2011, 309-316.
Zhong, et al., "Three Coordination polymers based on 1H-Tetrazole (HTz) generated via in Situ Decarboxylation: Syntheses, Structures, and Selective Gas Adsorption Properties", Crystal Growth & Design, vol. 10, No. 2, Mar. 2, 2010, 739-746.
Nugent et al., Porous materials with optimal adsorption thermodynamics and kinetics for CO2 separation, Nature, Mar. 7, 2013, 495, 80-84.

*Primary Examiner* — Edward M Johnson
(74) *Attorney, Agent, or Firm* — Billion & Armitage; Gregory S. Schwartz

(57) ABSTRACT

Embodiments include a metal-organic framework (MOF) composition comprising one or more metal ions, a plurality of organic ligands, and a solvent, wherein the one or more metal ions associate with the plurality of organic ligands sufficient to form a MOF with kag topology. Embodiments further include a method of making a MOF composition comprising contacting one or more metal ions with a plurality of organic ligands in the presence of a solvent, sufficient to form a MOF with kag topology, wherein the solvent comprises water only. Embodiments further include a method of capturing chemical species from a fluid composition comprising contacting a MOF composition with kag topology and pore size of about 3.4 Å to 4.8 Å with a fluid composition comprising two or more chemical species and capturing one or more captured chemical species from the fluid composition.

12 Claims, 22 Drawing Sheets

METHOD USING METAL-ORGANIC FRAMEWORK COMPOSITIONS

BACKGROUND

Gas/vapor separation represents a large share of processing in oil, petrochemical, nuclear and many other industries. Gas/vapor separation related to upstream and downstream of natural gas (NG) processing is often very complex and challenging, particularly at the stage of sweetening (removal of acid gases ($CO_2$, $H_2S$)), dehydration and BTX (Benzene, Toluene and Xylenes) removal.

The control of greenhouse gases is of societal importance because it is well recognized that it has a significant impact on climate change. Among all the greenhouse gas emissions, $CO_2$ has received the most attention due to the large quantities of man-made emissions in the atmosphere. The $CO_2$ atmospheric concentration has exploded to reach record levels in May 2013 of 400 parts per million (ppm), which is an unprecedented level in human history. For years, the scientific community has focused its efforts to develop different strategies to mitigate the undesirable $CO_2$ emissions in the atmosphere from industrial activities (particularly emissions of $CO_2$ originating from the burning of fossil fuels) and transportation. Therefore, $CO_2$ Capture and Storage (CCS) and $CO_2$ Capture and Use (CCU) are recognized as strategies to reduce the emissions of $CO_2$ from the atmosphere.

Among the handful of technologies that tackle this challenge, cryogenic distillation and liquid amine scrubbing are the dominant methods. Nevertheless, these technologies are highly energy intensive, hence not cost effective. Adsorption is currently recognized as one of the alternative separation technologies that can address capturing the $CO_2$ challenge, taking into account both technical and cost effectiveness. Therefore, the choice of the suitable adsorbents that drives the separation process is of prime importance. Many materials have been investigated for their properties to adsorb $CO_2$ selectively, which includes zeolites, carbon based materials and metal-organic frameworks.

SUMMARY

Embodiments of the present disclosure include a metal-organic framework (MOF) composition comprising one or more metal ions, a plurality of organic ligands, and a solvent, wherein the one or more metal ions associate with the plurality of organic ligands sufficient to form a MOF with kag topology.

Embodiments of the present disclosure further include a method of making a MOF composition comprising contacting one or more metal ions with a plurality of organic ligands in the presence of a solvent, sufficient to form a MOF with kag topology, wherein the solvent comprises water only.

Embodiments of the present disclosure also describe a method of capturing chemical species from a fluid composition comprising contacting a MOF composition with kag topology and pore size of about 3.4 Å to 4.8 Å with a fluid composition comprising two or more chemical species and capturing one or more captured chemical species from the fluid composition.

DETAILED DESCRIPTION

Figure 1:
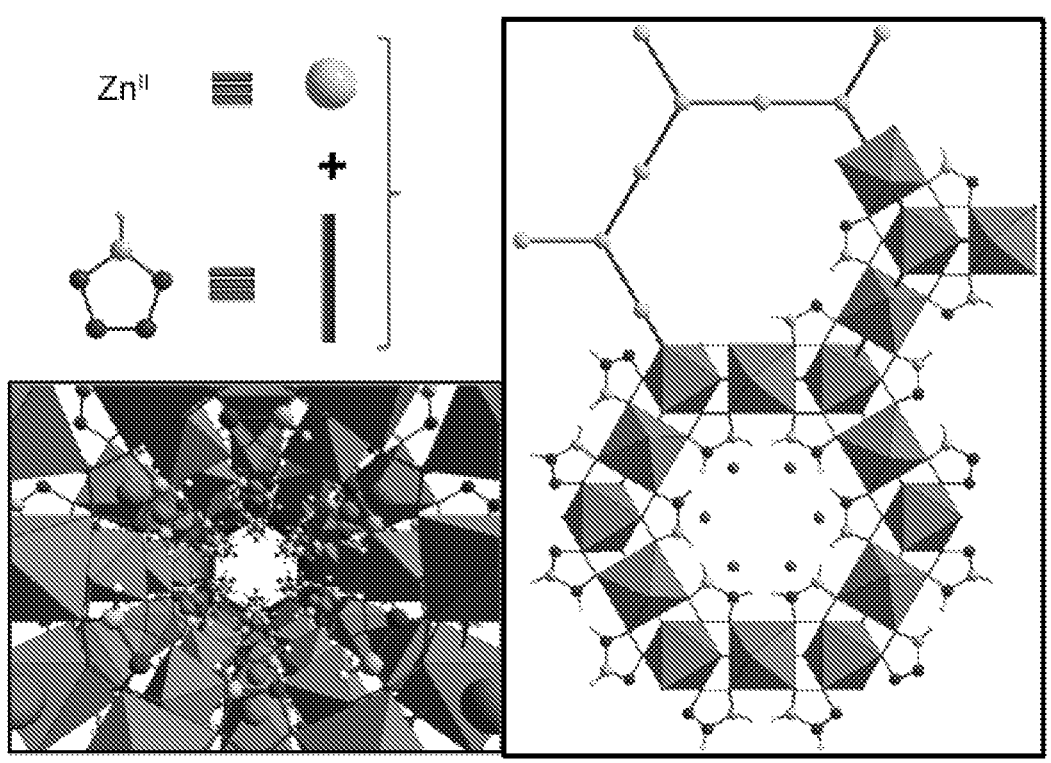
FIG. 1 illustrates a schematic representation of a 3D kagomé tilling network (color scheme: Zinc=cyan, Nitrogen=blue, Carbon=grey, Oxygen=red, Hydrogen=white), according to some embodiments.

In general, embodiments of the present disclosure describe metal organic framework compositions, and methods of making and using MOF compositions. In particular, the present disclosure describes embodiments including a highly stable metal organic framework composition fabricated in water without any other solvent and with a low-cost reagent, such as tetrazolate and zinc salts. This MOF platform is a highly stable, nitrogen-rich MOF made in water for multipurpose use in gas/vapor separations, such as dehydration, $CO_2$ capture, $H_2S$ removal and BTX sieving from natural gas. The MOFs of the present embodiments can be synthesized in water without any other solvent, with simple process steps and low-cost chemicals, such as zinc salt and tetrazolate based ligand. The MOF compositions of the present disclosure include a kagomé (kag) topology. The kag-MOF composition is highly stable and exhibits suitable properties for $CO_2$ from flue gas and natural gas in dry conditions. The compositions described herein show an excellent balance between selectivity, $CO_2$ uptake and energy for regeneration. Additionally, the compositions include desiccant properties, particularly with a low energy for dehydration. The kag-MOF compositions can also successfully and substantially perform $H_2S/CH_4$, $H_2S/BTX$ and acetone/phenol separation and gas dehydration.

Although many N-containing MOFs have been reported, systematic studies on $CO_2$ capture in concurrent correlation to pore size are scarce. Embodiments here describe efforts to tune/design novel materials for $CO_2$ capture, such as developing several strategies to enhance the $CO_2$ energetics in MOFs. As a first example, rht-MOF-7, fabricated by deliberate modification of the trigonal core of the parent rht-MOF-1 by a triazine core linked to an amine functional group in between the core and isopthalate termini, was found to be excellent candidate platforms for systematic enhancement of $CO_2$ capture efficiency. The resulting synergetic effect of N-containing ligand and secondary amine was reflected by a drastic enhancement of the isosteric heat of $CO_2$ adsorption at low loading (44.7 kJ $mol^{-1}$ versus 35 kJ $mol^{-1}$ for the parent rht-MOF-1), albeit with a subsequent sharp decrease, mainly because of the quick saturation of the highly energetic sites, but non-homogeneous, and the occurrence of pore filling which follows.

In a second example, the assembly of rare-earth based (terbium) fcu platform by utilizing polarized ligands containing tetrazolate and fluoro moieties positioning in a close vicinity of open metal sites, has resulted in very high $CO_2$ energetics as the initial $Q_{st}$ at low loading was 58.1 kJ $mol^{-1}$. Similar to the rht platform, the amount of highly energetic sites was limited and non-homogeneously distributed. In both cases, rht and fcu platforms possess quite big cavities (10.4 and 17.8 Å in the former and 14.5 and 9.1 Å, respectively), therefore the $CO_2$ adsorption occurs first on the most active (limited) sites which saturate quickly leading in turn to a drastic decrease in selectivity toward $CO_2$.

In another example, a reticular chemistry approach aiming to build an extended/contracted series of channel based MOFs constructed with bypiridyne/Cu and pyrazine/Zn 2-D periodic 4×4 square grids pillared by $SiF_6$ anions, led to the unveiling of an effective adsorption mechanism combining both thermodynamics and energetics. In fact, the contracted analogue assembled from zinc (or copper) cation and pyrazine ligand, characterized by channels with small pore diameter of 3.84 Å (SIFSIX-3-Zn), showed high and uniform $Q_{st}$ for $CO_2$ at 45-52 kJ $mol^{-1}$ throughout the loading, affording unprecedented physical adsorbent with high selectivity towards $CO_2$ at various concentrations. With this foundation, embodiments of the present disclosure are then directed to a new MOF material with small-channeled pores, assembled using nitrogen-rich polarizable ligand.

The kag-MOFs described herein can utilize green-synthesis methods for synthesizing porous materials, which reduce or eliminate the need for solvents and corrosive metal salt reagents, reduce or eliminate toxic and/or acidic byproducts, and are scalable to industrial levels. The future deployment of MOF materials at the larger scale for many applications such as adsorbents, catalysts, and sensors, among many others, require clean, environmentally friendly, easy, cost efficient and scalable synthesis procedures. Solution-based MOF synthesis methodologies, such as the solvothermal method previously discussed, suffer from the need to use toxic and/or corrosive metal salts reagents. In addition to being costly and hazardous, these reagents further generate acid byproducts, which are often susceptible to solvolysis and require costly disposal. The need for fresh solvents, enhanced safety precautions, and waste disposal greatly increases both the capital costs and production costs of these methods. Low reproducibility further precludes industrial applications of solvothermal synthesis methods.

Metal organic frameworks (MOFs) are a versatile and promising class of crystalline solid-state materials that allow porosity and functionality to be tailored towards various applications.

Generally, MOFs comprise a network of nodes and ligands, wherein a node has a connectivity capability at three or more functional sites, and a ligand has a connectivity capability at two functional sites each of which connect to a node. Nodes are typically metal ions or metal containing clusters, and, in some instances, ligands with node connectivity capability at three or more functional sites can also be characterized as nodes. In some instances, ligands can include two functional sites capable of each connecting to a node, and optionally one or more additional functional sites, which do not connect to nodes within a particular framework. In some embodiments, ligands can be poly-functional, or polytopic, and comprise two or more functional sites capable of each connecting to a node. In some embodiments, polytopic ligands can be heteropolytopic, wherein at least two of the two or more functional sites are different.

Embodiments of the president disclosure describe a metal-organic framework composition comprising one or more metal ions, an organic ligand, and a solvent, wherein the one or more metal ions associate with the organic ligand sufficient to form a MOF with kag topology. The one or more metal ions may include $M^{2+}$ cations. The $M^{2+}$ cations may include one or more of $Zn^{2+}$, $Cu^{2+}$, $Ni^{2+}$, $Co^{2+}$. The organic ligand may be an inexpensive organic building block. The organic ligand may include any N donor ligand. For example, the organic ligand may include one or more of tetrazole, triazole, derivatives of tetrazole, and derivatives of triazole. The one or more metal ions may associate with the organic ligand to form a metal-organic framework with kagomé topology (kag-MOF). (FIG. 1) In some embodiments, the kag-MOF includes a plurality of organic ligands. In some embodiments, the kag-MOF is formed in the presence of a solvent, wherein the solvent includes water or is only water. In some embodiments, the kag-MOF may be hydrothermally synthesized. In other embodiments, the kag-MOF may be highly stable. In another embodiment, the kag-MOF may be hydrothermally synthesized and highly stable.

The kag-MOF of the present disclosure may include any combination of $M^{2+}$ cations—including, but not limited to, one or more of $Zn^{2+}$, $Cu^{2+}$, $Ni^{2+}$, and $Co^{2+}$— with any combination of organic ligands—including, but not limited to, one or more of tetrazole, triazole, derivatives of tetrazole, and derivatives of triazole. In some embodiments, the kag- MOF may include one of the above-mentioned metal cations or a mixture of metal cations, with one of the above-mentioned organic ligands, a mixture of organic ligands, a plurality of the above-mentioned organic ligands, or a plurality of a mixture of organic ligands.

Embodiments of the present disclosure also include methods of making a MOF composition. The method of making a MOF composition may include contacting one or more metal ions with an organic ligand sufficient to form a MOF with kag topology. In other embodiments, the method of making a MOF composition may include contacting one or more metal ions with a plurality of organic ligands sufficient to form a MOF with kag topology. In another embodiment, the method of making a MOF composition may include contacting one or more metal ions with an organic ligand or a plurality of organic ligands in the presence of a solvent. In some embodiments, the solvent includes water or is water only.

Embodiments of the present disclosure further include a method of capturing chemical species from a fluid composition. The method may include contacting a MOF composition with kag topology and pore size of about 3.4 Å to 4.8 Å with a fluid composition comprising two or more chemical species and capturing one or more captured chemical species from the fluid composition. The MOF composition with kag topology may include any of the embodiments described above. The chemical species captured by the kag-MOF may include one or more of $CO_2$, $H_2S$, $H_2O$, and acetone. In some embodiments, $CO_2$ is the captured chemical species from a fluid composition including one or more of natural gas, flue gas, syngas, biogas, and landfill gas. In other embodiments, $H_2S$ is the captured chemical species from a fluid composition including one or more of $H_2S$, benzene, toluene, and xylene. In other embodiments, $H_2O$ is the captured chemical species from a fluid composition including one or more of a gas, a vapor, and a solvent. In other embodiments, acetone is the captured chemical species from a fluid composition including one or more of acetone, phenol, and $C_4$ fractions. These embodiments are not limiting, and additional embodiments are provided below.

The kag-MOF described in these embodiments exhibits high chemical and thermal stability based on the kagomé platform. The particular synergetic effect of highly dense, homogeneously distributed tetrazoles, zinc cations and small pore size of channels, directed the homogeneous and fairly high interactions with $CO_2$, in one example. Embodiments herein confirm the high importance of the synergy between at least two driving forces, namely N-rich containing ligand and small pore size, to achieve the desired materials for capturing $CO_2$, $H_2S$, $H_2O$, and acetone. Owing to its facile hydrothermal synthesis, stability and structural properties, applications may utilize this kagomé platform-based MOF as a membrane for various gas separations based on molecular sieving effect.

Figure 2A:
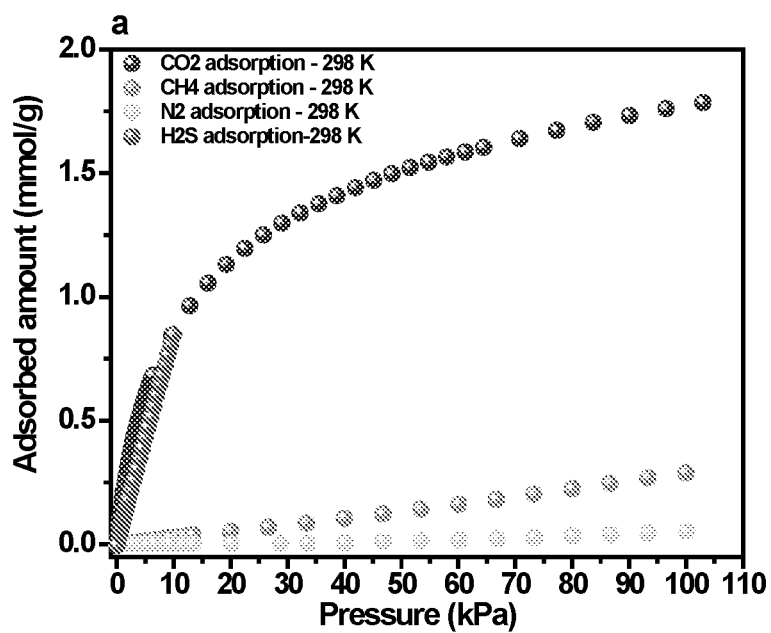
FIGS. 2A-B illustrate graphical views of (A) Adsorption of $CO_2$, $H_2S$, $CH_4$ and $N_2$ on kag-MOF, (B) isosteric heat of adsorption of $H_2O$ vapour, $CO_2$ and $CH_4$, according to some embodiments.

The kag-MOF of the present disclosure exhibited high chemical and hydrothermal stability. The synergetic effect of the charges densely and uniformly distributed over the pore channels (FIG. 1) and contracted pore size ranging from about 3.4 Å to 4.8 Å led to quite strong and steady $CO_2$ isosteric heat of physical adsorption translated into highly uniform $CO_2$ interaction within the framework, a key feature that directs the efficiency of $CO_2$ capture using adsorbents in dry conditions (FIG. 2). As seen from FIG. 2a, the measurement of $H_2S$ up to 0.1 bar (partial pressure) shows that the steepness of the adsorption isotherm in case of $H_2S$ is almost similar to $CO_2$, the $H_2S$ in this case is adsorbed strongly and reversibly. $H_2S$ adsorbs preferentially over $CO_2$ using kag-MOF.

Figure 2B:
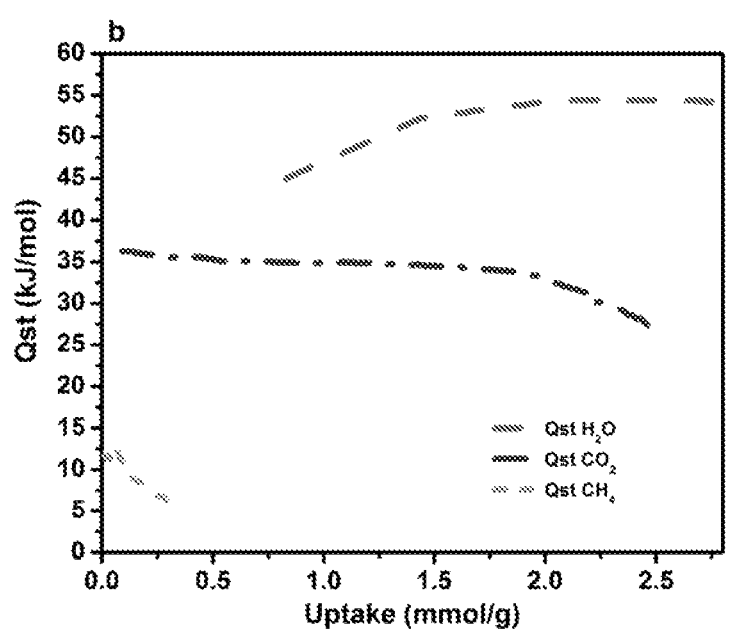
Figure 3:
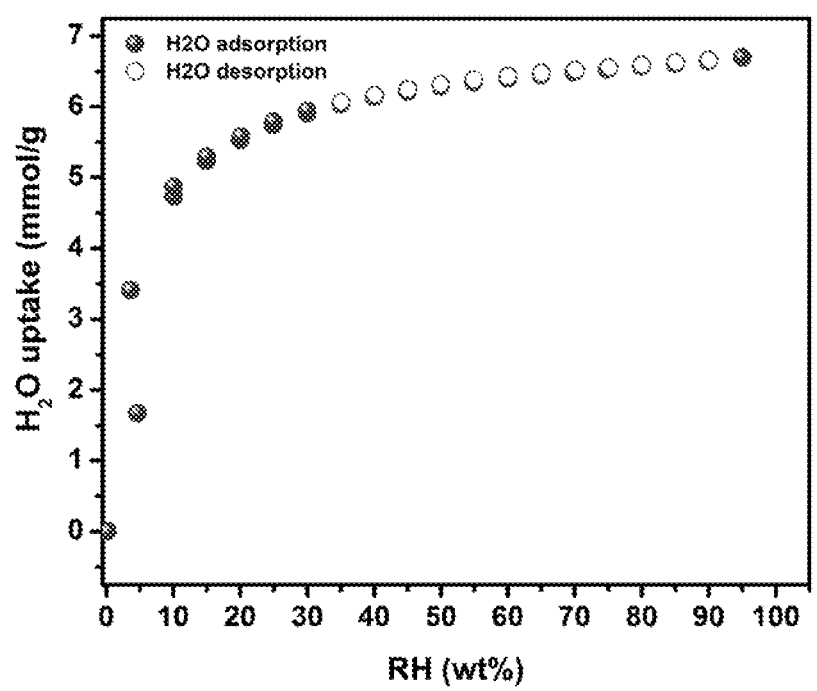
FIG. 3 illustrates a graphical view of adsorption of $H_2O$ on kag-MOF at 298K after evacuation at 393 K, according to some embodiments.

The heat of adsorption of $CO_2$, $CH_4$ and $H_2O$ shows that $H_2O$ interacts strongly (58 kJ/mol) with the framework of kag-MOF as compared to $CO_2$ (36 kJ/mol) and $CH_4$ (12.5 kJ/mol) (FIG. 2b). Therefore, it is expected that kag-MOF could be used also as an efficient gas dehydration agent (FIG. 3) for industrial gases such as natural gas (NG). The best performing conventional materials for gas dehydration are 4 Å and 13X zeolites. For these zeolites, the energy necessary for reactivation (and subsequent recycling) is twice as much (ca. 120 kJ/mol) as kag-MOF. This finding is important as dehydration of gases is a very energy intensive process and there is a large need for new dehydration agents to reduce the cost of water removal from industrial gases.

Figure 15A:
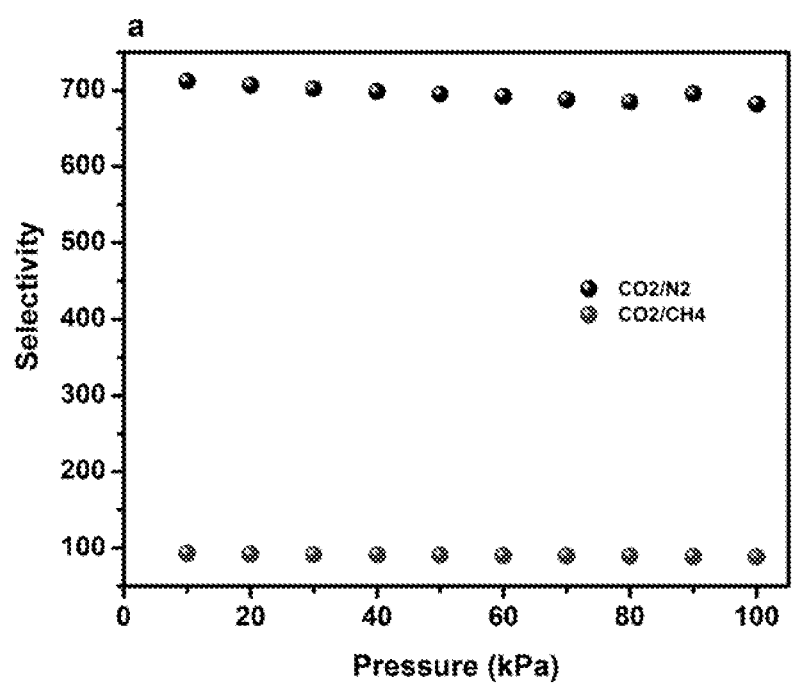
FIGS. 15A-B illustrate a graphical views of (A) IAST prediction for $CO_2/N_2$, $CO_2/CH_4$ mixtures, (B) Column breakthrough test for $CO_2/N_2$:10/90 mixture adsorption at 298 K and 1 bar total pressure, according to some embodiments.
Figure 15B:
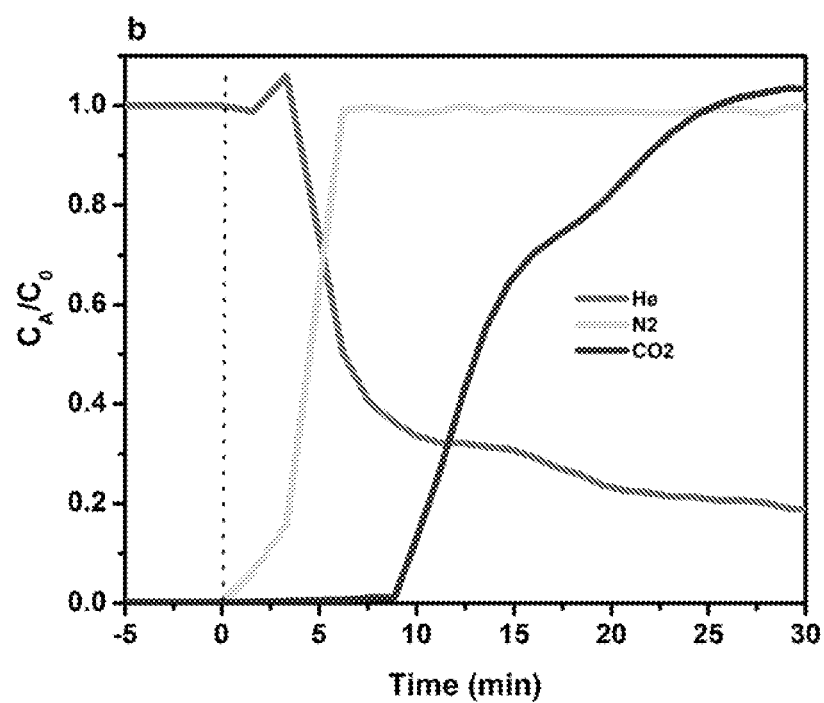

Once the $CO_2$ containing stream was water vapor and $H_2S$ free, the kag-MOF was an excellent separation agent for $CO_2$ removal from flue gas and natural gas. This was confirmed experimentally using column breakthrough test performed using $CO_2/N_2$:10/90 mixture (FIGS. 15A-B). In fact, while $CO_2$ was retained in the column for 601 s, the first $N_2$ signal was observed just after 2 s, indicative of the high $CO_2$ selectivity (520±200).

Figure 4:
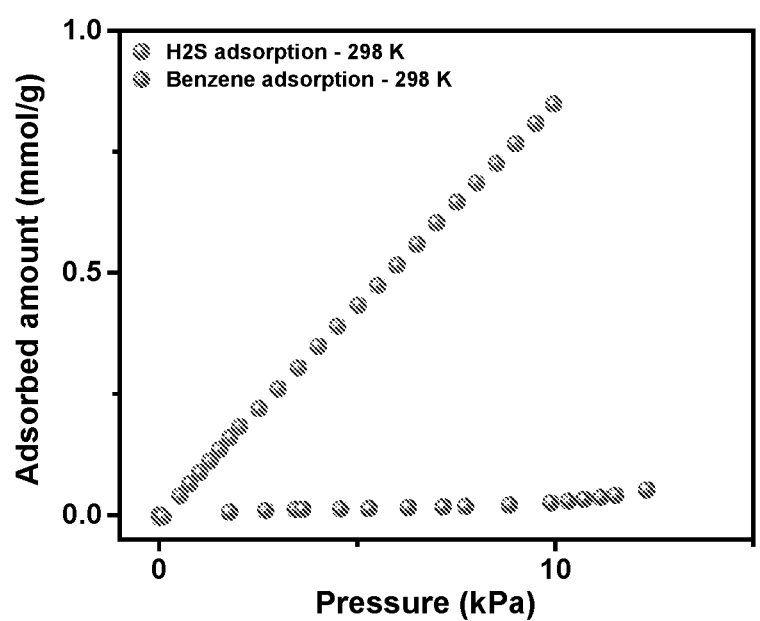
FIG. 4 illustrates a graphical view of adsorption of $H_2S$ as compared to benzene on kag-MOF at low pressures (No benzene is adsorbed), according to some embodiments.

In light of the high $H_2S$ adsorption capacity and the small channel size (aperture) of kag-MOF, the adsorption of benzene (one of the components of the undesirable BTX in natural gas) was studied to evaluate its equilibrium adsorption properties as compared to $H_2S$. Interestingly, benzene was shown not to adsorb on kag-MOF. See FIG. 4, for example, illustrating a graphical view of adsorption of $H_2S$ as compared to benzene on kag-MOF at low pressures, according to an embodiment of the present disclosure. This second finding shows that kag-MOF can potentially be used to sieve $H_2S$ from BTX (Benzene, Toluene, Xylene).

Because of the sieving features of kag-MOF for benzene, it is believed that kag-MOF will be an excellent agent for the important separation of acetone from phenol and acetone from $C_4$.

Embodiments of the present disclosure include using kag-MOF compositions for $H_2S$ removal from NG. The particular outstanding properties of kag-MOF materials in terms of stability, $H_2S$ uptake and selectivity make this novel MOF suitable for many industrial applications where $H_2S$ need to be removed, particularly NG which is of the extreme importance for the Kingdom of Saudi Arabia.

Embodiments of the present disclosure include using kag-MOF compositions for dehydration. The particular outstanding properties of kag-MOF in terms of stability to moisture, $H_2O$ uptake and affinity make these series of novel MOFs suitable for many industrial applications where various degree of humidity need to be removed.

As discussed above, embodiments of the present disclosure include using kag-MOF compositions for $CO_2$ capture from NG. kag-MOF may be used as an efficient adsorbents for the removal of $CO_2$ at various concentration (from 1% to 20%) from dry and humid conditions relevant to industrial gases.

Embodiments of the present disclosure include using kag-MOF compositions for $H_2S$/BTX separation. The presence of aromatics such as benzene, toluene and xylene (BTX) as contaminants in $H_2S$ gas stream entering Claus sulfur recovery units has detrimental effect on catalytic reactors, where BTX form soot particles, and clog and deactivate the catalysts. BTX removal before the BTX and $H_2S$ containing stream enter the catalyst bed, could be a judicious solution to this problem. Because of the sieving affinity and it extremely high stability, kag-MOF may be used as a separation agent on PTSA (pressure-temperature swing system).

Embodiments of the present disclosure include using kag-MOF compositions for acetone/phenol and acetone/$C_4$ separation. The sieving property of kag-MOF for benzene inspired to launch a study for the separation of acetone from Phenol and $C_4$ fractions. kag-MOF is a potential material for this separation.

Example: $CO_2$ Capture

The novel kagomé metal organic framework (MOF) with small pore size and N-rich linker was synthesized hydrothermally via coordination of tetrazole moieties with zinc cations which shows high chemical and thermal stability, as an example. The synergetic effect of the charges densely and uniformly distributed over the pore channels and contracted pore size led to quite strong and steady $CO_2$ isosteric heat of adsorption translated into highly uniform $CO_2$ interaction within the framework, a key feature that direct the efficiency of $CO_2$ capture using adsorbents.

MOFs represent a class of porous materials that offer high surface areas, permanent porosity and chemical tunability, making these materials suitable for adsorbing $CO_2$. However, designing stable MOFs with high selectivity towards $CO_2$ adsorption is still a challenging task. In fact, the affinity to $CO_2$ compared to other gases ($N_2$, $CH_4$, $O_2$, etc.) is one of the key factors influencing the economy of the $CO_2$ capture process. Hence, it is vital to tailor the functionality and the pore size of MOFs simultaneously in order to design novel materials specifically dedicated to $CO_2$. Intensive efforts are currently invested in the search of new strategies allowing the enhancement of binding energies between $CO_2$ molecules and the framework. (i) Incorporation of Lewis basic sites into MOFs (eg: amino groups), (ii) insertion of open metal sites and (iii) introduction of various other strongly polarizing functional groups are three approaches that are most the frequently strategies explored.

Figure 5:
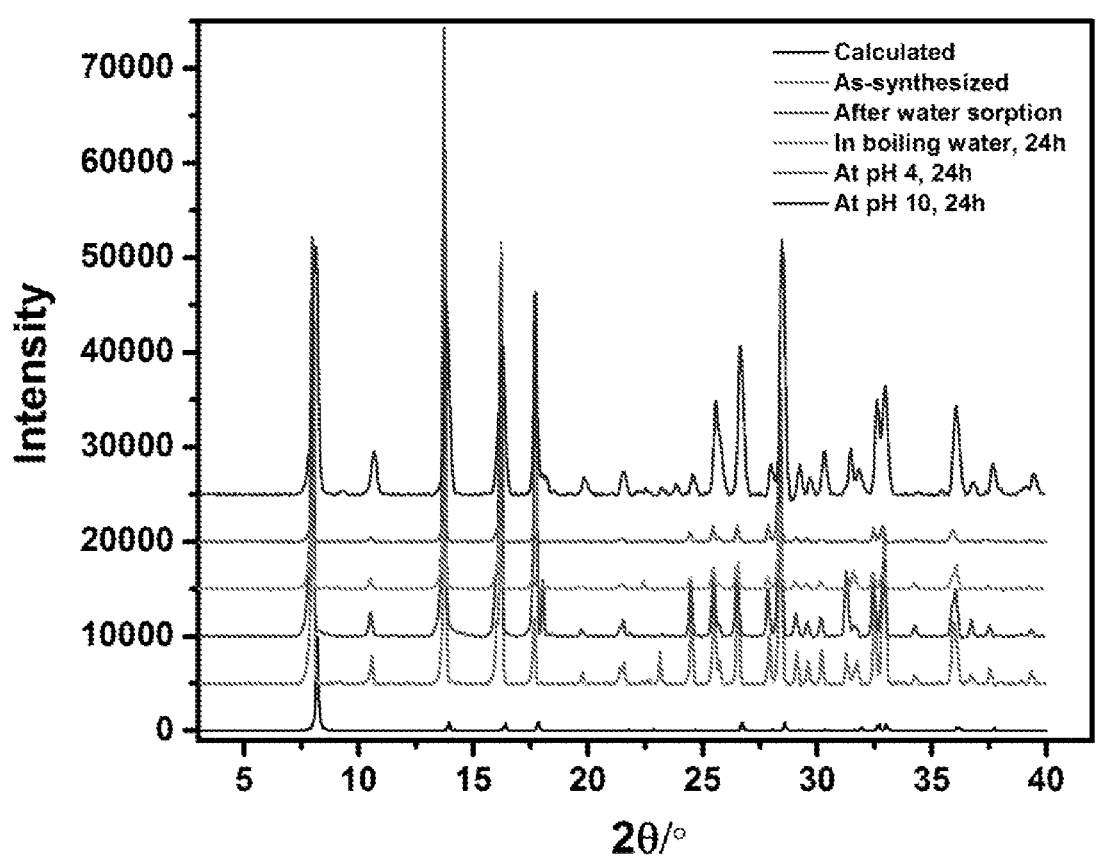
FIG. 5 illustrates a graphical view of experimental and calculated powder X-ray diffraction patterns indicating the phase purity and stability of kag-MOF at different thermal and chemical conditions, according to some embodiments.
Figure 6:
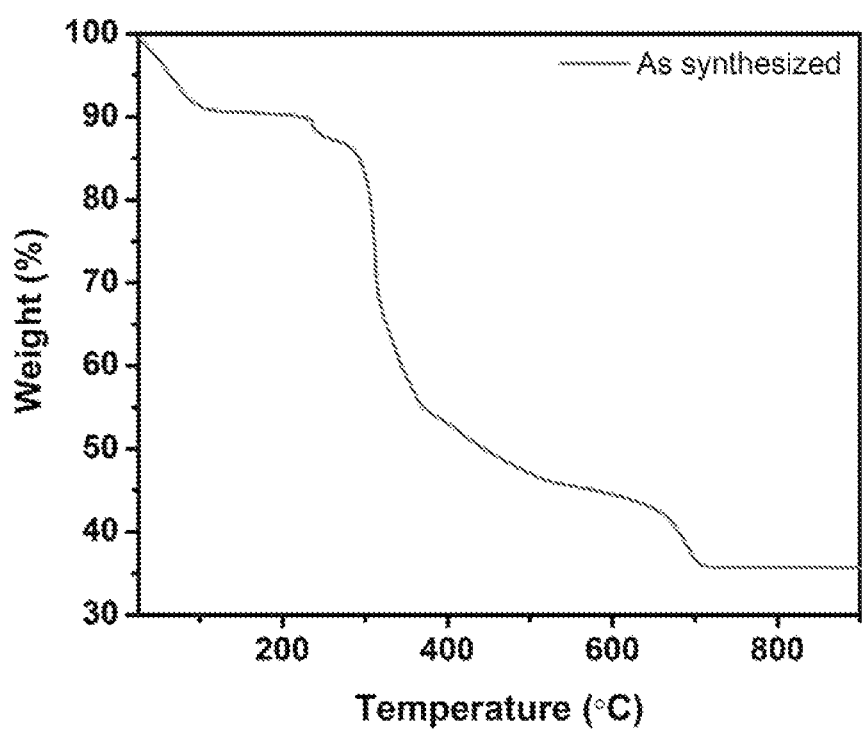
FIG. 6 illustrates a graphical view of TGA of kag-MOF, according to some embodiments.
Figure 7:
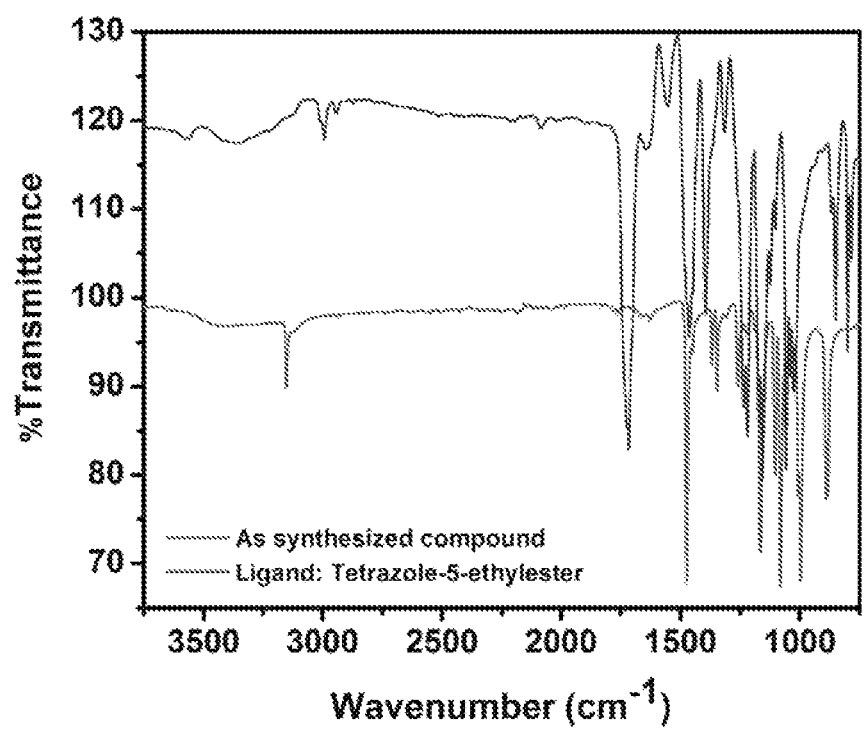
FIG. 7 illustrates a graphical view of comparison of IR spectrum of the as-synthesized kag-MOF vs ligand, according to some embodiments.

Indeed, hydrothermal reaction between $Zn(NO_3)_2 \cdot 3H_2O$ and tetrazole-5-carboxylate, ethyl ester yields a homogenous microcrystalline material. The as synthesized compound was characterized and formulated by single crystal X-ray diffraction studies as $Zn_5(HTet)_6(Tet)_3(OH^-)_7$. The purity of the material was confirmed by similarities between simulated and experimental powder X-ray diffraction (PXRD) (FIG. 5) and elemental microanalysis. The crystallographic analysis states that a de-esterification occurs during the reaction. To confirm this contention, thermogravimetric analysis (TGA) was carried out under air (FIG. 6) and the residue was analyzed by PXRD. The TGA shows two main drops corresponding to a total loss of 64.4% which is in good agreement with the theoretical data (62.1%). In addition, infrared spectroscopy measurements performed on the ligand clearly showed the presence of the ester group, with the characteristic $v_{c=o}$ band (1735 $cm^{-1}$) and the absence of the $v_{c=o}$ band of esters in the kag-MOF indicating the in situ de-esterification of the ligand during the synthesis. (FIG. 7).

The compound crystallized in a hexagonal system (space group P6$_3$/mmc) and contained two crystallographic independent zinc cations, both coordinated to six nitrogen atoms of two independent tetrazole ligands to form octahedral surrounding. Neutral and deprotonated tetrazole ligands adopt tridentate and tetradentate coordination modes respectively. The assembly of the 6-connected Zn(1) nodes and neutral tetrazole molecules result in the generation of 2D kagomé layers exhibiting hexagonal channels (FIG. 8(a)).

Figure 8:
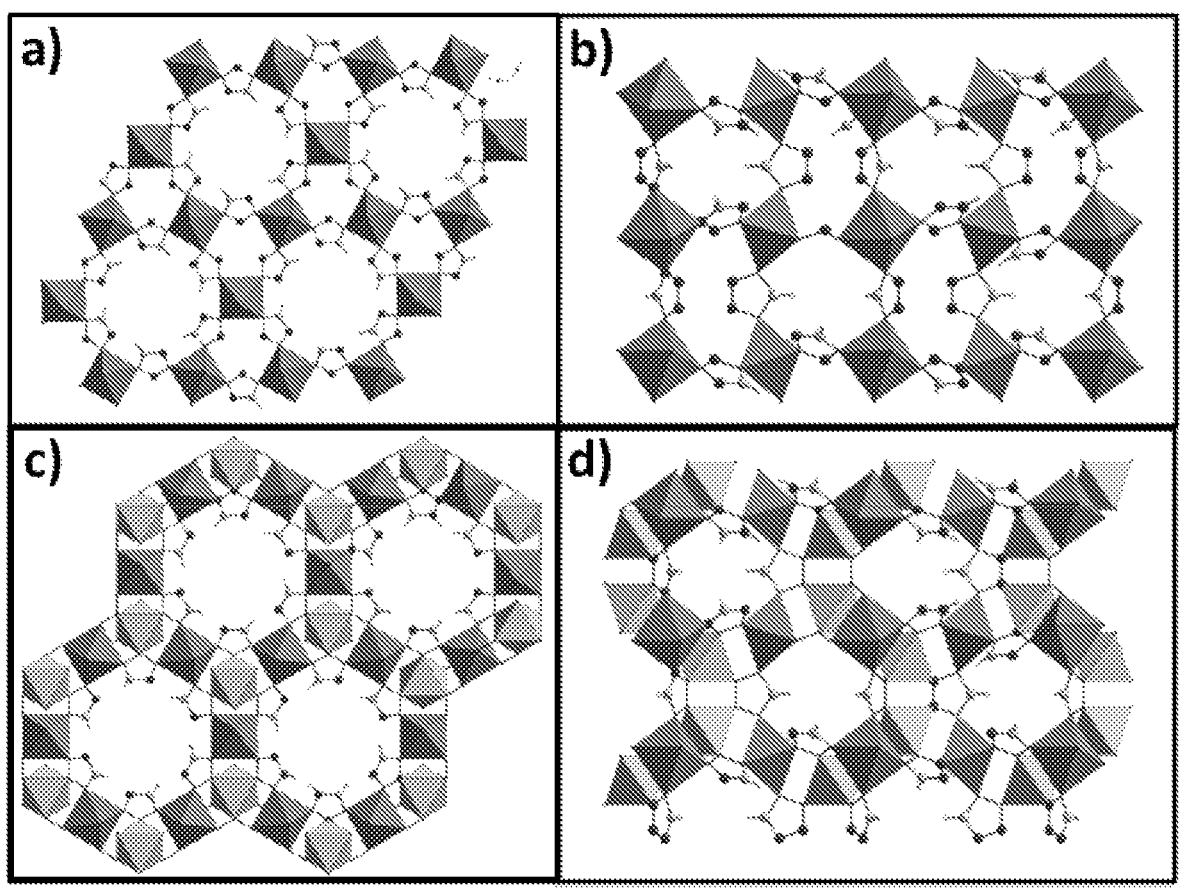
FIGS. 8A-D illustrate schematic representations of 2D kagomé tilling networks, according to some embodiments.

The packing of these layers along the c axis following the axial-to-axial pillaring, using Zn(2) cations and deprotonated tetrazolates, yield a cationic 3D structure, balanced by hydroxide anions, with an overall kagomé tilling (kag) geometry (FIG. 8). The framework exhibits 1D hydrophobic channels with a diameter of around 3.8 Å (FIG. 1).

FIG. 8 describes (a) projection along (001) of the kagomé layer built up from Zn(1) cations and neutral tetrazol molecules; (b) projection along (010) showing the packing of kagomé layers via deprotonated tetrazole molecules; (c) and (d) projection along (001) and (010) respectively of the structure showing the introduction of Zn(2) cations within the structure.

Figure 9:
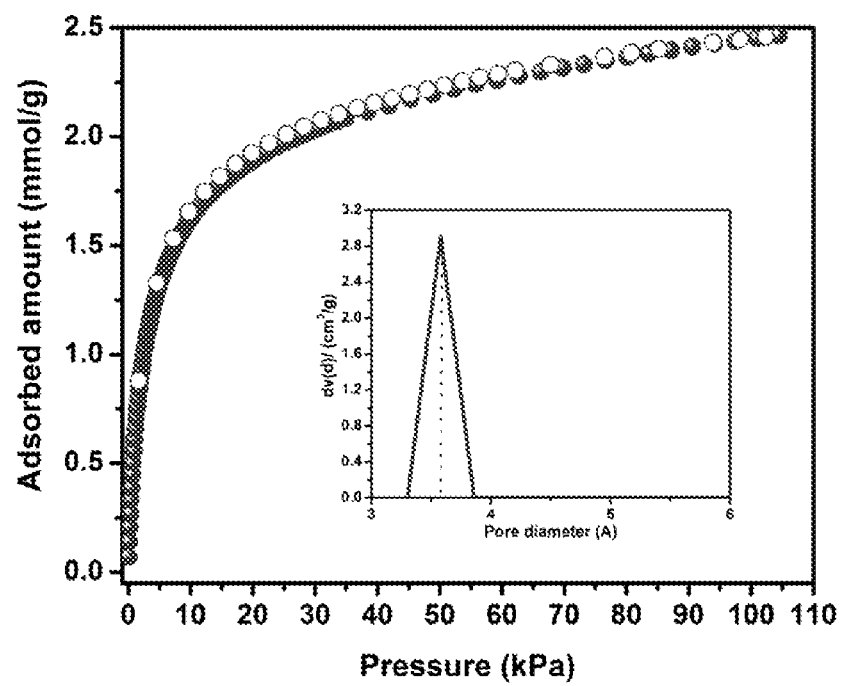
FIG. 9 illustrates a graphical view of $CO_2$ adsorption (filled circles)-desorption (open circles) isotherm on kag-MOF at 273 K (evacuation at 393 K). The inset shows the pore size distribution determined using NLDFT, according to some embodiments.

Initial adsorption studies showed that $N_2$ and Ar probe the framework of the compound as non-porous at 77 and 87 K, respectively. This first result confirms, that indeed, the pore windows of this material are narrow, as was concluded from single crystal diffraction data. Accordingly, $CO_2$ measurement at 273 K was targeted as a primary methodology to confirm the permanent microporosity, as evidenced by the (fully reversible) type I $CO_2$ adsorption isotherm (FIG. 9).

The specific BET surface area was estimated to be 211 $m^2 \cdot g^{-1}$ using $CO_2$. The calculated theoretical total free pore volume was estimated to be 0.12 $cm^3 \cdot g^1$. The pore size distribution, calculated from $CO_2$ adsorption data at 273 K using non-Local density functional theory (NLDFT), was estimated to be very uniform, centered at diameter of 3.6 Å (FIG. 9), in excellent agreement with single crystal diffraction data.

Figure 10:
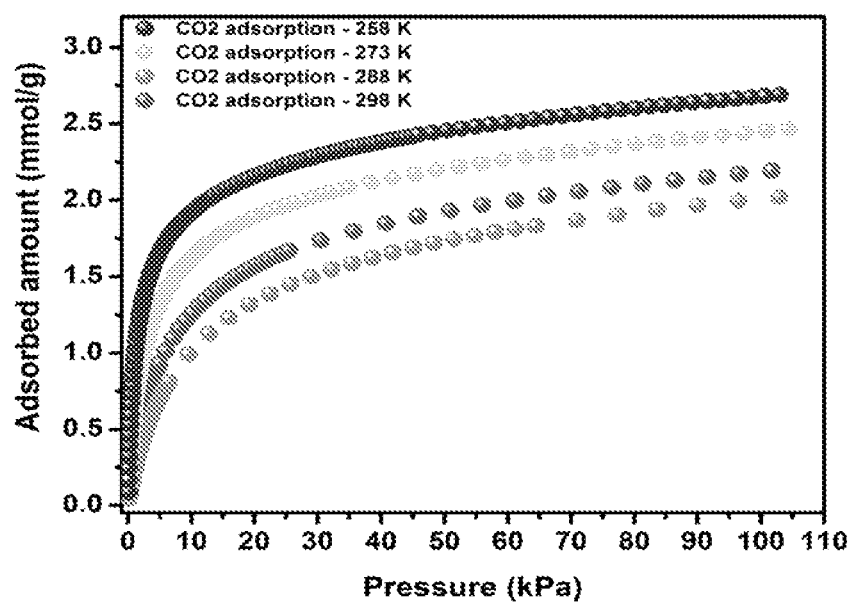
FIG. 10 illustrates a graphical view of variable temperature isotherms on kag-MOF after evacuation at 393K, according to some embodiments.
Figure 11:
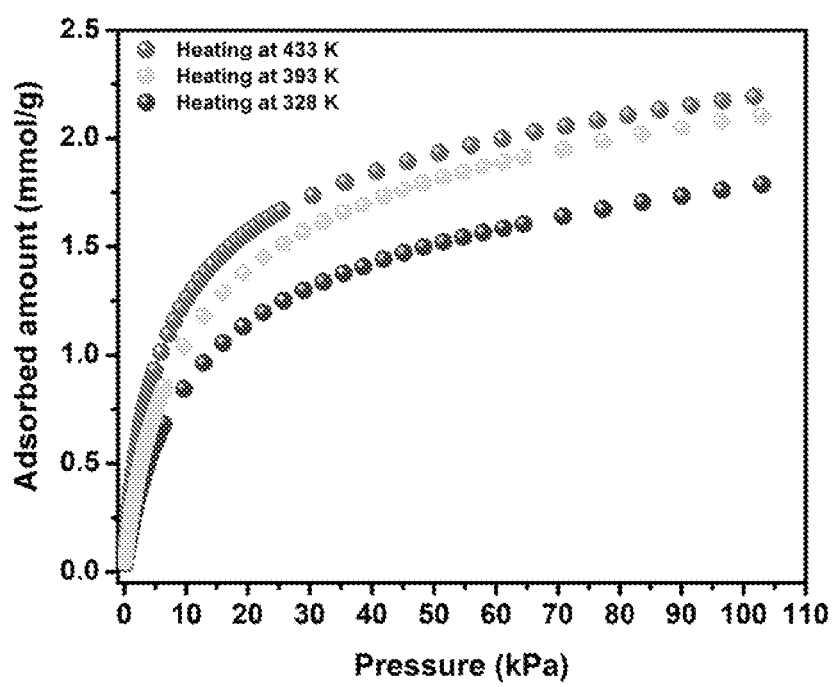
FIG. 11 illustrates a graphical view of $CO_2$ adsorption isotherms on kag-MOF at 298 K after evacuation at 328, 393 and 433 K, according to some embodiments.

The uniformly distributed, exposed tetrazole combined with the reduced pore size of kag-MOF, are attractive features for evaluating the impact of pore size, shape and functionality on $CO_2$ adsorption energetics and uptake. Accordingly, $CO_2$ adsorption experiments were carried out at various adsorption and desorption temperatures (FIG. 10) in order to look closely at the effect of total and partial evacuation of the framework on the $CO_2$ uptake and energetics. Prior to full adsorption study, optimization of activation protocol showed that kag-MOF can be fully evacuated at 393 K and further evacuation at 433 K resulted only a slight increase in the $CO_2$ uptake, particularly at 1 bar (FIG. 11).

Figure 12:
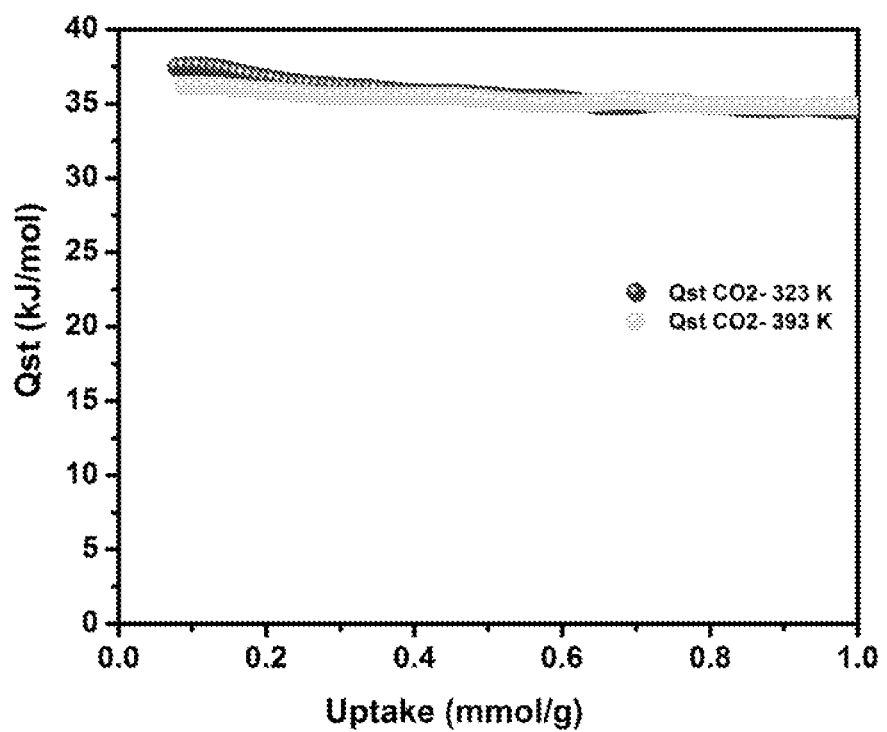
FIG. 12 illustrates a graphical view of $Q_{st}$ of $CO_2$ adsorption on kag-MOF after evacuation at 323 and 393 K, according to some embodiments.
Figure 13:
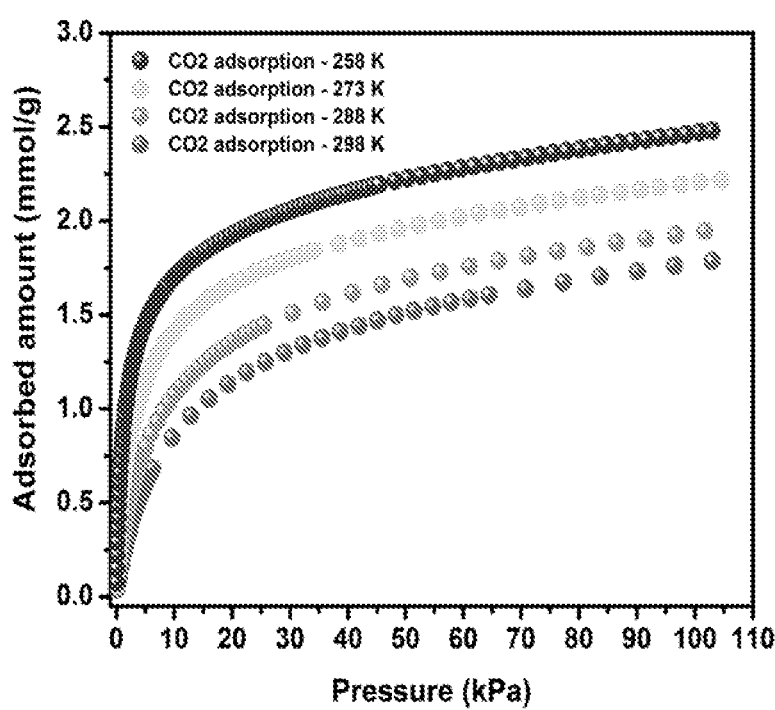
FIG. 13 illustrates a graphical view of variable temperature $CO_2$ adsorption isotherms on kag-MOF after evacuation at 323 K, according to some embodiments.

The isosteric heat of $CO_2$ adsorption, $Q_{st}$, was in turn calculated for the sample evacuated at 323K, 393 K (FIG. 12). The Clausius-Clapeyron equation was used to process the adsorption data collected at temperatures between 258 and 298 K (FIG. 13). Although a slight difference was observed in terms of uptake, the trends of the $CO_2$ $Q_{st}$ as a function of loading were found to be similar after evacuation at 328 and 393 K (FIG. 11). It is worth mentioning that the accuracy of the $Q_{st}$ determination was confirmed by the established linearity of $CO_2$ isosters for the entire studied range of $CO_2$ loadings.

Figure 14:
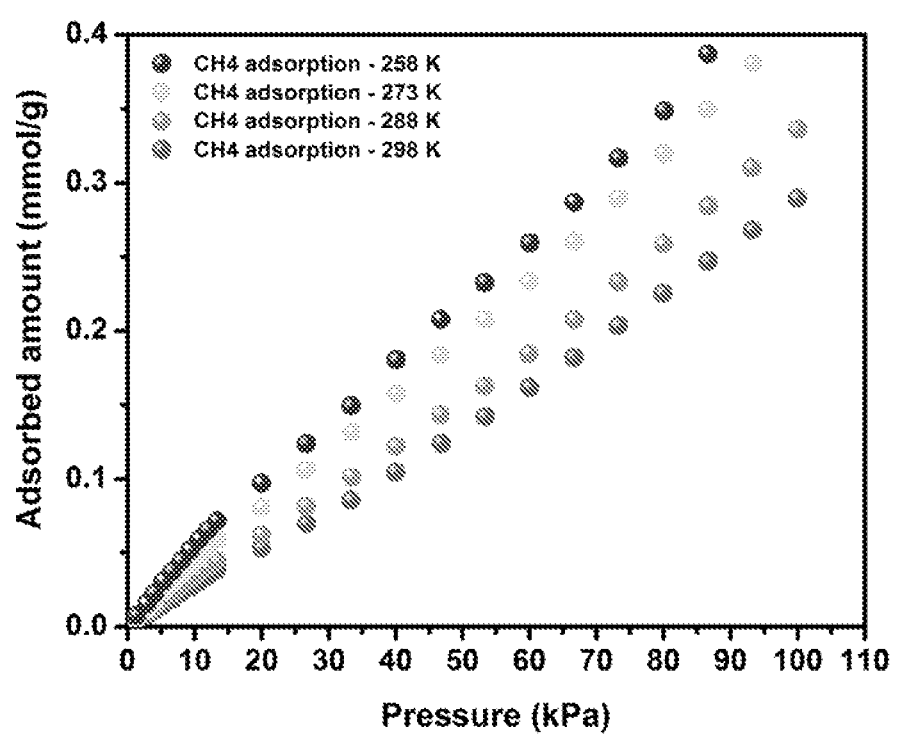
FIG. 14 illustrates a graphical view of variable temperature $CH_4$ adsorption isotherms on kag-MOF after evacuation at 393 K, according to some embodiments.

The $Q_{st}$ of $CO_2$ adsorption is an intrinsic property that dictates the affinity of the pore surface toward $CO_2$, which in turn plays a major role in determining the adsorption selectivity and the necessary energy to release $CO_2$ during the regeneration step. As illustrated, kag-MOF exhibits quite high $CO_2$ affinity over a wide range of $CO_2$ loading (37.5 kJ·mol$^{-1}$) due to the homogenously distributed strong adsorption sites. In light of the direct relationship of $CO_2$ and $CH_4$ adsorption energetics to $CO_2/CH_4$ adsorption selectivity, the $Q_{st}$ of $CH_4$ adsorption was explored, determined from variable temperature $CH_4$ adsorption isotherms (FIG. 14). In contrast to $CO_2$ energetics, $CH_4$ exhibits much lower $Q_{st}$ at low loading (12.5 kJ·mol$^{-1}$) combined with decreasing trend as the uptake increased.

Figure 16A:
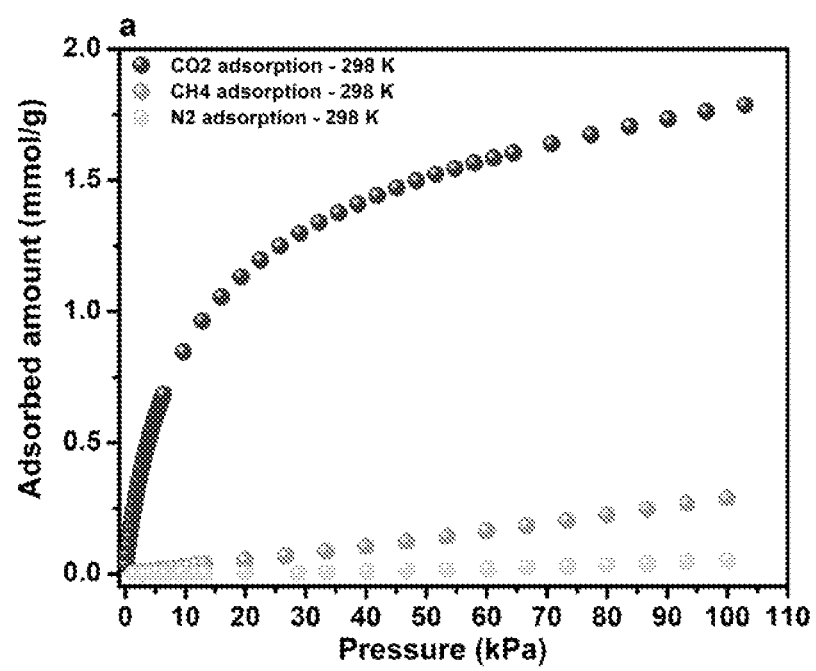
FIGS. 16A-B illustrate graphical views of (A) pure component $CO_2N_2$, $CH_4$ at 298K (B) $Q_{st}$ of $CO_2$ and $CH_4$ adsorption after activation at 55° C. and 120° C., according to some embodiments.
Figure 16B:
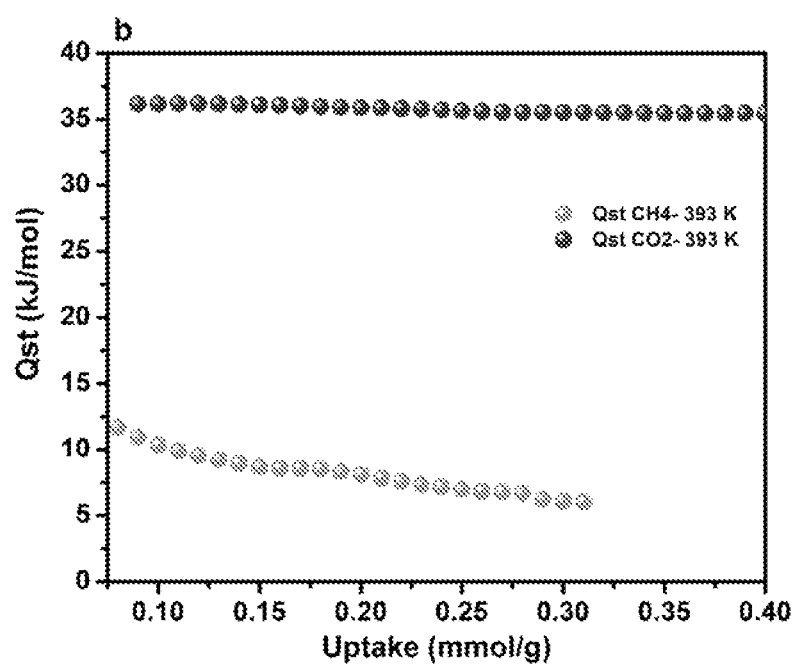

Elevated and uniform $CO_2$ interactions are the key to improve selectivity towards $CO_2$, which is a critical parameter for the effectiveness of gas separation and purification of important commodities from $CO_2$ (e.g., $CH_4$, $N_2$, $H_2$). Analysis of data using IAST (FIGS. 15A-B), shows that this material displays high $CO_2/N_2$ selectivity (ca. 700 at 1 bar for example) over a wide range of pressure while the calculated $CO_2/CH_4$ selectivity (88 at 1 bar) was comparatively low. In case of $CO_2/N_2$ mixture, the low $N_2$ adsorption uptake/energetics, translated into low affinity for $N_2$ (FIG. 15A) combined with the relatively strong energetics of $CO_2$ adsorption (FIGS. 16A-B), results in high equilibrium adsorption selectivity toward $CO_2$ (FIG. 15B).

This result was confirmed experimentally using column breakthrough test performed using $CO_2/N_2$:10/90 mixture. In fact, while $CO_2$ was retained in the column for 601 s, the first $N_2$ signal was observed just after 2 s, indicative of the high $CO_2$ selectivity (520±200), which is in quite good agreement with the predicted results using IAST.

Figure 17:
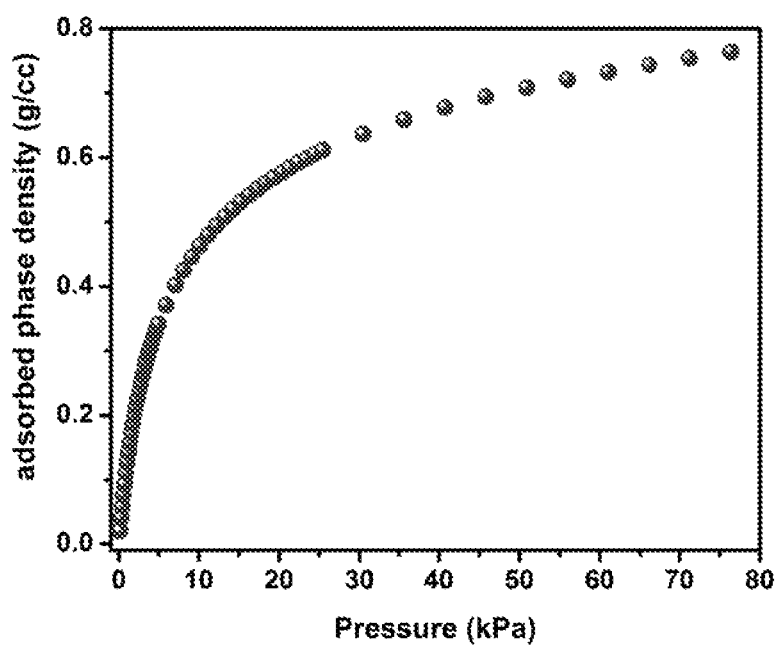
FIG. 17 illustrates a graphical view of Density of $CO_2$ adsorbed at 298 K, according to some embodiments.

It is noteworthy to mention that the $CO_2$ uptake (volumetric and gravimetric) at the partial pressure of interest for post-combustion (1.26 mmol/g and 0.84 mmol/g at 0.1 bar for single gas and $CO_2/N_2$:10/90 mixture, respectively) is much lower for kag-MOF than the corresponding $CO_2$ uptake for the best MOF materials reported so far such as Mg-MOF-74, and SIFSIX-3-M. Nevertheless, the recorded density of $CO_2$ adsorbed phase is one of the highest for MOFs (FIG. 17).

Figure 18:
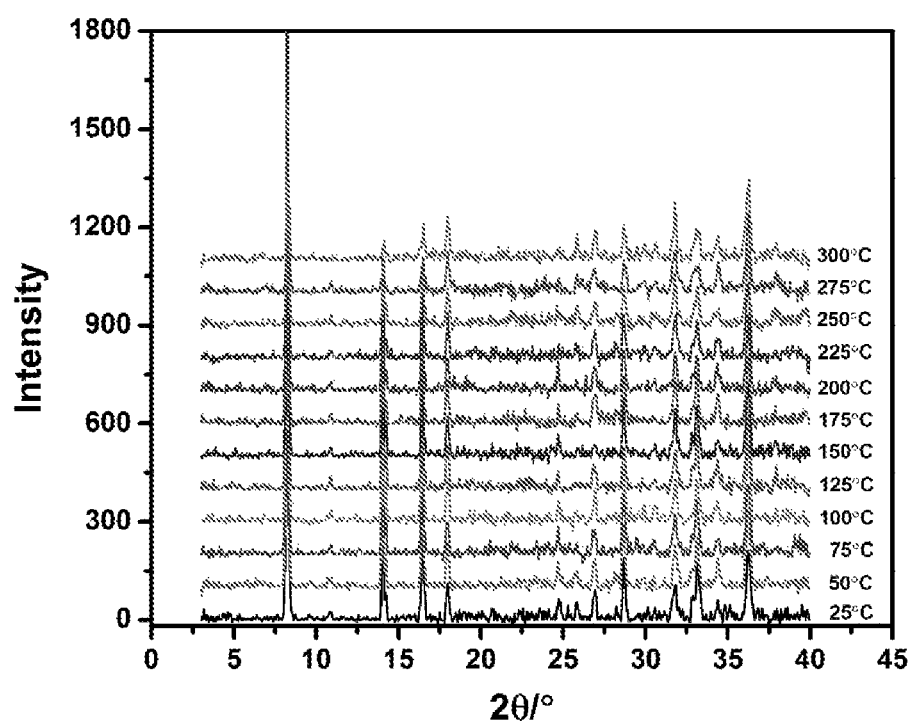
FIG. 18 illustrates a graphical view of Variable Temperature PXRD patterns of kag-MOF, according to some embodiments.
Figure 19:
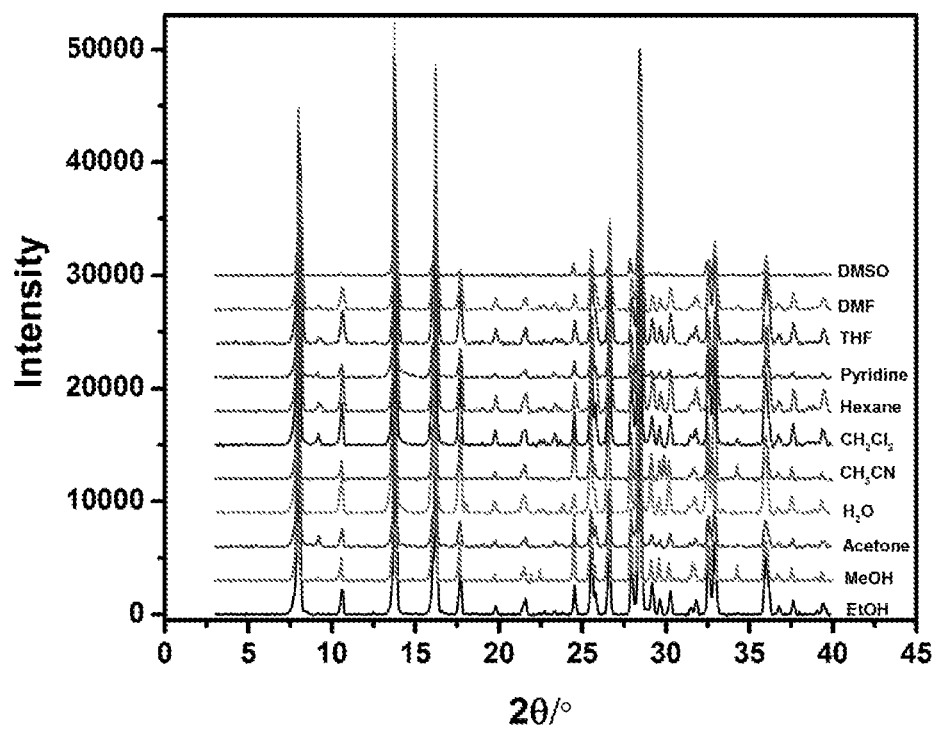
FIG. 19 illustrates a graphical view of PXRD patterns of kag-MOF after soaking in different solvents for 24 h as evidence of the stability of kag-MOF, according to some embodiments.

In addition to the efficiency of $N_2$ and $CH_4$ separation from $CO_2$, improving hydrothermal and chemical stability of MOFs in order to implement them in real-world conditions is another primordial ongoing key challenge for many MOFs. The thermal stability of the kag-MOF was evaluated using powder X-ray diffraction (PXRD) and maintains its crystallinity upon heating to temperatures up to 400° C. (FIG. 18). The same outstanding stability was observed after 24 h soaking in water, boiling water, at different pH (FIG. 5) and other organic solvents (FIG. 19). All these results in addition to the rare hydrothermal nature of synthesis of kag-MOF confirm the exceptional thermal and chemical stability of the kag-MOF.

Experimental Methods: Synthesis of $Zn_5(HTet)_6(Tet)_3(OH^-)_7$

A solution containing $Zn(NO_3)_3 \cdot 6H_2O$ (29.7 mg, 0.1 mmol), Tetrazole-5-ethylester (32.8 mg, 0.2 mmol), 4 ml $H_2O$ was prepared in a Teflon lined autoclave and heated to 160° C. for 24 h. Colorless crystals were harvested and air dried (Yield: 45%). Elemental Analysis for calculated formula $Zn_5(HTet)_6(Tet)_3(OH—)_7$: C=11.04% (theo.: 10.08%), H=2.01% (2.07%), N=45.94% (47.02%).

Single Crystal X-Ray Diffraction

TABLE 1

| Crystal data and structure refinement | |
| --- | --- |
| Empirical formula | $C_9H_9N_{36}O_7Zn_5$ |
| Formula weight | 1060.37 |
| Temperature | 150(2) K |
| Wavelength | 1.54178 Å |
| Crystal system, space group | Trigonal, P –3 1 c |
| Unit cell dimensions | a = 12.478(1) Å c = 12.708(1) Å |
| Volume | 1713.6(5) Å$^3$ |
| Z, Calculated density | 2, 2.055 |
| Absorption coefficient | 4.741 mm$^{-1}$ |
| F(000) | 1042 |
| Crystal size | 0.340 × 0.205 × 0.069 mm |
| Theta range for data collection | 4.09° to 66.83° |
| Limiting indices | –14 <= h <= 14, –14 <= k <= 14, –14 <= l <= 12 |
| Reflections collected/unique | 17668/969 [R(int) = 0.0542] |
| Completeness to theta = 66.83 | 94.5% |
| Absorption correction | Semi-empirical from equivalents |
| Max. and min. transmission | 0.7528 and 0.6451 |
| Data/restraints/parameters | 969/0/89 |
| Goodness-of-fit on F^2 | 1.054 |
| Final R indices [I > 2sigma(I)] | $R_1$ = 0.0729, $wR_2$ = 0.2330 |
| R indices (all data) | $R_1$ = 0.0746, $wR_2$ = 0.2367 |
| Largest diff. peak and hole | 1.860 and –2.248 e.Å$^{-3}$ |

What is claimed is:

1. A method of capturing chemical species from a fluid composition, the method comprising
   contacting a metal organic framework (MOF) composition with a kag topology with a fluid composition comprising $H_2S$, $CO_2$, or acetone; and
   capturing the $H_2S$, $CO_2$, or acetone from the fluid composition;
   wherein the MOF composition comprises ligands, wherein the ligands include one or more of tetrazole, triazole, derivatives of tetrazole, and derivatives of triazole.

2. The method of claim 1, wherein the MOF composition includes one or more of $Zn^{2+}$, $Cu^{2+}$, $Ni^{2+}$, and $Co^{2+}$ metal ions.

3. The method of claim 1, wherein capturing includes adsorbing the $H_2S$, $CO_2$, or acetone by the metal organic framework.

4. The method of claim 1, wherein the MOF composition is used as a separation agent in a pressure-temperature swing system.

5. The method of claim 1, wherein a pore size of the MOF composition ranges from about 3.4 Å to about 4.8 Å.

6. The method of claim 1, wherein the fluid composition further includes one or more of $H_2S$, benzene, toluene, and xylene.

7. The method of claim 1, wherein the fluid composition further includes one or more of natural gas, flue gas, syngas, biogas, and landfill gas.

8. The method of claim 1, wherein the fluid composition further includes water.

9. The method of claim 8, wherein the water is also captured from the fluid composition.

10. The method of claim 1, wherein the fluid composition further includes one or more of acetone, phenol, and C4 fractions.

11. The method of claim 1, wherein the fluid composition is in a gas or vapor phase.

12. The method of claim 1, wherein a BET surface area of the MOF composition is about 200 m$^2 \cdot$g$^{-1}$.

* * * * *